United States Patent [19]
Whittaker

[11] Patent Number: 5,869,606
[45] Date of Patent: Feb. 9, 1999

[54] AMINO ACIDS PEPTIDES OR DERIVATIVES THEREOF COUPLED TO FATS

[75] Inventor: Robert George Whittaker, New South Wales, Australia

[73] Assignee: Commonwealth Scientific and Industrial Research Organisation, Campbell, Australia

[21] Appl. No.: 477,698

[22] Filed: Jun. 7, 1995

Related U.S. Application Data

[62] Division of Ser. No. 396,299, Feb. 28, 1995, Pat. No. 5,583,198, which is a continuation of Ser. No. 853,779, Jun. 9, 1992, abandoned.

[30] Foreign Application Priority Data

Dec. 22, 1989 [AU] Australia ................................. PJ8035

[51] Int. Cl.$^6$ .................................................. C07K 1/113
[52] U.S. Cl. ..................... 530/345; 530/324; 530/325; 530/326; 530/327; 530/328; 530/329
[58] Field of Search .................................. 530/812, 345, 530/402, 324, 325, 326, 327, 328, 329; 554/36, 1

[56] References Cited

U.S. PATENT DOCUMENTS

| | | | |
|---|---|---|---|
| 4,314,048 | 2/1982 | Doi et al. | 528/44 |
| 4,751,219 | 6/1988 | Kempen | 514/26 |
| 5,019,383 | 5/1991 | Hopp | 424/88 |

FOREIGN PATENT DOCUMENTS

| | | |
|---|---|---|
| B-28694/89 | 7/1989 | Australia . |
| 168263 | 1/1986 | European Pat. Off. . |
| 217643 | 4/1987 | European Pat. Off. . |
| 0 329 295 | 1/1988 | European Pat. Off. . |
| 0 325 160 | 7/1989 | European Pat. Off. . |
| 3633175 | 4/1987 | Germany . |
| 54-043731 | 4/1979 | Japan . |
| 62-103643 | 5/1987 | Japan . |
| WO 93/02706 | 2/1993 | WIPO . |

OTHER PUBLICATIONS

Chemical Abstracts, vol. 65, No. 3, 5616c.

Whitakker, R.G. and Bender, V.J. "A New Procedure for Coupling Peptides with Fats", *Proceedings of the Second International Conference on Solid Phase Synthesis and Related Technologies*, pp. 495–498.

Bender, V.J. et al. "Using TRIS to Couple Peptides with Fats", *Proceedings of the Seventeenth Annual Conference on Protein Structure and Function*, Lorne, Feb. 1992.

Reilly, W. et al. "An LHRH Pili Based Vaccine Adjuvanted with a Novel Fatty Acid Adjuvant: A Possible Alternate Immunological Approach for the Treatment of Prostate and Breast Cancers", *Keystone Symposium on Cellular Immunity and Immunotherapy of Cancer*, Taos, New Mexico, Mar. 17–24, 1993.

Bender, V.J. et al. "Delivery Studies Using Peptide–Fatty Acid Conjugates", *Thirteenth American Peptide Symposium*, Edmonton, Alberta, Canada, Jun. 20–25, 1993.

Reilly, W. et al. "LHRH Fatty Acid Admixture Vaccines: An Alternate Immunological Approach for the Treatment of Hormone Dependent Prostate and Breast Cancers", *Australian Society of Experimental Pathology*, Melbourne, Australia, Sep./Oct. 1993.

Whittaker, R.G. et al. "A Gentle Method for Linking Tris to Amino Acids and Peptides", *Peptide Research*, 6(3) (1993):125–8.

"Chemical Abstracts", vol. 102, No. 3, Jan. 21, 1985, p. 735.

Kashima, C., Amino Alcohols as C–Terminal Protecting Groups in Peptide Synthesis:, *Journal of the Chemical Society*, Perkin Transactions I, Mar. 1988, pp. 535–539.

Bender, V.J. et al. "Using TRIS for Coupling Peptides with Fats", *Proc. 36th Ann. Conf. Aust. Soc. Biochem. Mol. Biol.*, Melbourne, 1992.

*Primary Examiner*—Douglas W. Robinson
*Assistant Examiner*—Anish Gupta
*Attorney, Agent, or Firm*—McDermott, Will & Emery

[57] ABSTRACT

The present invention provides novel compounds in which peptides, amino acids or derivatives thereof are bound to other molecules, in particular fatty acids, which facilitate the use of such peptides, amino acids or derivatives thereof. The basic structure of the compounds of the present invention are an amino acid, peptide or derivative thereof linked to 1 to 3 fatty acid molecules via a tromethamine derivative. Alternatively, the amino acid, peptide or derivative thereof may be linked to a fatty acid by an ethanolamine derivative.

5 Claims, 4 Drawing Sheets

AMINO ACIDS PEPTIDES OR DERIVATIVES THEREOF COUPLED TO FATS

This application is a division of application Ser. No. 08/396,299 filed Feb. 28, 1995, now U.S. Pat. No. 5,583, 198, which is a continuation of application Ser. No. 07/853,779, filed Jun. 9, 1992, now abandoned.

The present invention relates to novel compounds in which peptides, amino acids or derivatives thereof are bound to other molecules which facilitate the use of such peptides, amino acids or derivatives thereof.

In recent years there have been substantial advances made in the area of developing biological reactive peptides and peptide based compounds. One of the main difficulties encountered in the use of such compounds is the absence of an effective delivery system. It has been shown that antibodies raised against small peptides are active against large proteins (e.g. foot and mouth virus), however, such small peptides are rarely antigenic in the absence of an appropriate adjuvant.

The present inventor has discovered a novel means by which peptides and/or amino acid(s) and peptide derivatives may be linked to other molecules which may facilitate the therapeutic use of such peptides, amino acids or derivatives thereof. In addition, the present inventor has produced novel compositions having these characteristics.

Accordingly, in a first aspect the present invention consists in a compound of the following formula:

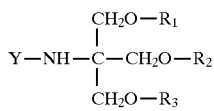

in which Y represents an amino acid, peptide or derivative thereof and $R_1$, $R_2$ and $R_3$ are the same or different and are either hydrogen or fatty acids.

In a second aspect the present invention consists in compound of the following formula:

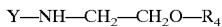

in which Y represents an amino acid, peptide or derivative thereof and $R_4$ represents hydrogen or a fatty acid.

As will be recognised by persons skilled in the art the compound of the first aspect of the present invention consists of an amino acid, peptide or derivative thereof linked to a tromethamine derivative to which is optionally linked a fatty acid(s). Similarly, the compound of the second aspect can be recognised as an amino acid, peptide or derivative thereof linked to an ethanolamine derivative to which is optionally linked a fatty acid.

In a preferred embodiment of the first aspect of the present invention, each of $R_1$, $R_2$ and $R_3$ are a fatty acid, and more particularly, are each the same fatty acid. It is presently preferred that the fatty acid has a carbon chain of 3 to 18 carbon atoms, more preferably 10 to 18 carbon atoms, most preferably 16 carbon atoms. In the same manner, it is preferred that $R_4$ is a fatty acid having a carbon chain of 3 to 18 carbon atoms, more preferably 10 to 18 carbon atoms, and most preferably 16 carbon atoms.

In a further preferred embodiment of the first and second aspects of the present invention Y is cysteine. It is believed that cysteine in this position would be used to create a generic reagent(s) that could be coupled to free cysteines in proteins, peptides or derivatives thereof using standard cross linking reagents.

The novel compounds of the present invention enable alternative presentation of an amino acid, peptide or derivative thereof due to its position of attachment of fatty acids. Some of the potential uses of the novel compounds of the present invention are:

1. Immune enhancing affects of fatty acid-peptide conjugates. A large amount of research has been conducted into the potentiation of the immune response using fatty acid-peptide complexes. It is known that the presence of fatty acids does lead to an enhanced immune response to the peptide (Baschang, 1989, Tetrahedron, 45:6331–6360; Floc'h et al, 1984, Drugs Future, 9: 763–776; Jung et al, 1985 Angewandte Chemie Int. Ed. Eng. 24 (10) pp872–873).

2. Slow release delivery of peptides. Liposomes have been used as delivery and slow release vectors. (Moroder and Muriol, 1989, in Peptides Chemistry, Structure and Function, J. E. Rivier & G. R. Marshall Eds pp 811–812). Attaching fatty acids to peptides would help their incorporation into liposomes as well as be a method of incorporating peptides into "oily depots". (U.S. Pat. No. 4,829,142; Gregoriadis, 1989, in Targeting of Drugs: Implications in Medicine, F. H. D. Roerdinl & A. M. Kroon Eds pp 1–29).

3. Altering the mechanism of action. (De Vrije et al 1990, J. Mol Microbiol., 4: 143–150). Fatty acids attached to peptide hormones etc. could alter their biological activity e.g. by prolonging biological half life.

4. Fats are absorbed intact from the digestive system. It is possible that a peptide/fatty acid complex could be administered orally to deliver bioactive peptides and/or antigenic peptides.

5. Tromethamine (TRIS) in general has a variety of industrial uses including an emulsifying agent for cosmetic creams and lotions. Therapeutically used as an alkalizer (merch Index, Vol 11, entry 1536). It is possible that some of these uses could be improved by the addition of amino acids or peptides optionally with fatty acids (Molinero et al 1988, JAOCS, 65: 975–978).

The present inventors envisage that by attaching peptides or peptide derivatives by their C-terminal to either TRIS-tripalmitate (or other mono, di or tri constructs with various fatty acids) or amino acid-TRIS-fatty acid constructs it will be possible to facilitate interaction of the peptides-fats with a variety of lipid structures (both natural and artificial) e.g. liposomes of various types, cell walls, membranes etc. (ethanolamine and similar compounds may be used in place of TRIS). By this manner alternative methods can be derived for the delivery and in vivo presentation of peptides and for modifying their mode of action and antigenicity. For example, the use of synthetic antigens in various veterinary and human pharmacology still sets the very important problem of finding a suitable and inexpensive carrier devoid of side effects. Carriers used in animal trials, such as keyhole limpet haemocyanin (KLH), bovine serum albumin, ovalbumin and the tetanus toxoid are generally unsuitable for human application due to side effects such as immunogenicity. In addition some of them (e.g. KLH) have the additional problem of being very expensive.

Potentially more acceptable synthetic substitutes have been investigated by a number of laboratories.

The full chemical synthesis of the N-terminal lipopeptide of the outer membrane of E. coli has been described by G. Jung and his collaborators (Bessler et al 1984, Biochem. Biophys. Res. Comm. 121, pp55–61 and Jung 1988 "Low Molecular weight Lipopeptide Carrier-Adjuvant Systems for Immunisations: Developments and Results" in Peptide Chemistry T. Shiba and S. Sakakibara Ed. p.751–758) and intensive studies of the various peptide conjugates have been described. These compounds consist of three fatty acid molecules linked to S-(dihydroxypropyl) cysteine attached to a tetrapeptide of the sequence Ser-Ser-Asn-Ala. This type of construct and analogues of it have mitogenic activity and can used to anchor a variety of biological agents in lipid membranes.

A completely synthetic, low molecular weight vaccine against foot and mouth disease virus (FMDV) was developed in this manner (Weismuller et al 1989, Vaccine 1, pp29–33). A sequential epitope of FMDV surface glycoprotein (135–154) coupled to the tripalmitoyl-s-glyceryl-cysteinyl-serine-serine moiety induced long lasting high protection against foot and mouth disease after a single administration without any adjuvant or carrier. Similarly, a vaccine against influenza virus has been prepared (Deres et al 1989. Nature 342, pp561–564).

Other biological effects noted for this type of construct include the induction of cytotoxic T lymphocytes (Deres et al, as above), the release of cytokines such as interferon and tumour necrosis factor alpha from macrophages (Hauschildt et al 1990. Eur. J. Immunol. 20, pp63–68) and the activation of neutrophils (Seifert et al 1990. Biochem. J. 267, pp795–802).

A second novel oligopeptide delivery system for poorly absorbed peptides and drugs has been described by Toth et al 1989 ("A Novel Oligopeptide Delivery System for Poorly Absorbed Peptides and Drugs" in Peptides, Chemistry, Structure and Function, pages 1078–1079). This system is based on the development of synthetic, non natural amino acids with long alkyl side-chains; so called "fatty amino acids".

The covalent attachment of these compounds to various drugs has been reported to have increased oral absorption as well as overcoming the limited passage of e.g. GABA across the blood-brain barrier.

TRIS and ethanolamine seem to be ideal bi-functional molecules to join peptides (via their carboxyl group to the $NH_2$ group of TRIS or ethanolamine) and fats (via ester linkage to the hydroxyl group(s) of TRIS or ethanolamine). To demonstrate the feasibility of this approach several amino acids and peptides have been reacted with TRIS and the products characterised. Four of these, Z-Ala-TRIS, Z-Gly TRIS, Z-Leu-TRIS and BOC-Ala-Ile-Phe-TRIS were successfully palmitoylated and purified. As well as constructs of 2-Ala-TRIS with sloster chain fatty acids. After removal of the N-protecting group, the free amino terminal would be available to react with other amino acids or peptides either by enzymatic procedures or by traditional methods of peptide chemistry.

In order that the nature of the present invention may be more clearly understood preferred forms thereof will now be described with reference to the following examples and Figures in which.

Figure 5:
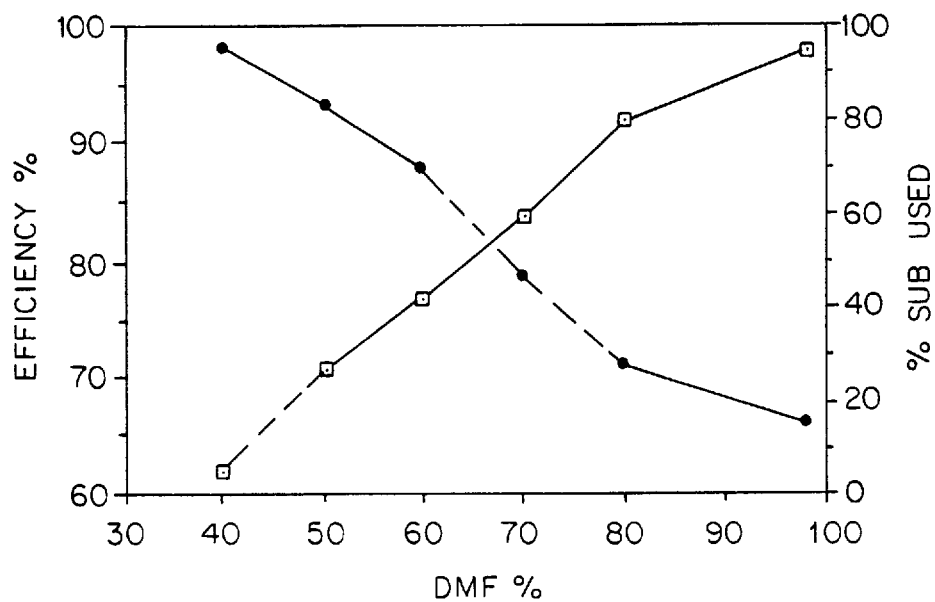
Figure 6:
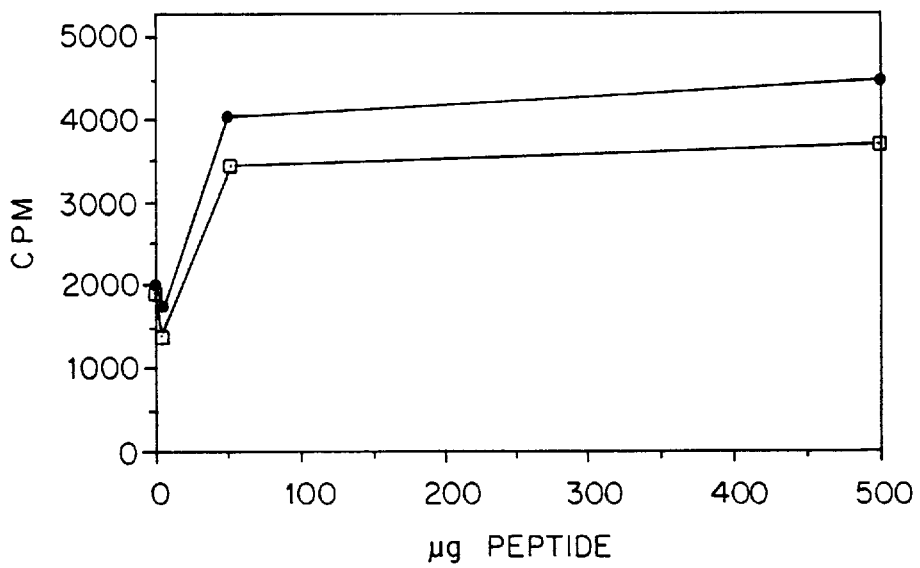
Figure 7:
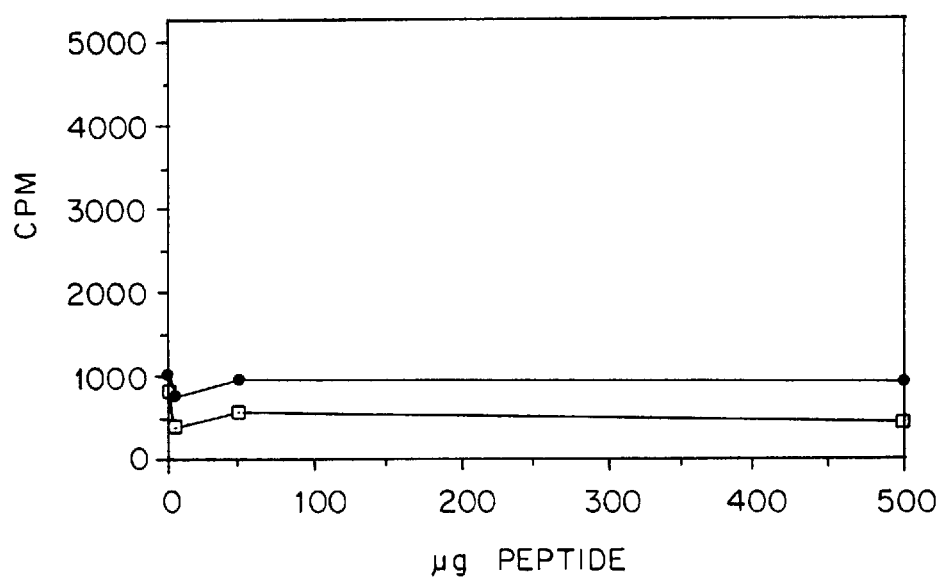

FIG. 5 DMF profile Z-Ala-TRIS; pH 9 incubated 2 days 60%C (— —□— —) efficiency; (—♦—) percentage substrate used;

FIG. 6 shows $^3$H-thymidine uptake in RD10 cells (— —□— —) ATP3; (—♦—) ZATP3; and FIG. 7 shows $^3$H-thymidine uptake in U937 cells (— —□— —) ATP3; (—♦—) ZATP3.

MATERIALS AND METHODS

Abbreviations:

| | |
|---|---|
| TLC | Thin layer chromatography |
| HPLC | High Performance Liquid Chromatography |
| NMR | Nuclear Magnetic Resonance |
| GLC | Gas-liquid chromatography |
| DCM | Dichloromethane |
| DCC | Dicyclohexylcarbodiimide |
| DCU | Dicyclohexylurea |
| DMAP | Dimethylaminopyridine |
| DMF | Dimethyl formamide |
| Z | Benzyloxycarbonyl |
| Bz | Benzoyl |
| BOC | Tertiary butyloxycarbonyl |
| TRIS | Tromethamine |
| OMe, OEt, OBzl | Methyl, Ethyl and Benzyl esters resp. |
| Ala, Leu, Gly, | The amino acids:- alanine, leucine, |
| Ile, Phe, Tyr, | glycine, isoleucine, phenylalanine, |
| Arg, Trp, Lys & | tyrosine, arginine, tryptophan, lysine |
| Val | and valine respectively |

A. CHEMICAL AND ANALYTICAL METHODS

All solvents were analytical reagents and those used for HPLC were especially purified for liquid chromatography.

THIN LAYER CHROMATOGRAPHY i) Plates:

a) Pre-coated TLC plates, Silica gel 60 (without fluorescence indicator, Merck 5721) 20×20 cm, 0.25 mm thickness.

b) TLC aluminium sheets, silica gel coated (with fluorescence indicator) DC Alufolien Kieselgel 60 20×20 cm, 0.2 mm thickness, Merck 5554.

c) TLC aluminium sheets, pre-coated with cellulose (20× 20 cm, 0.1 mm thickness, Merck 5552).

ii) Detection of compounds:

a) Ninhydrin 0.1% (Merck ARt, 6758)

b) 2,4 dichlorofluorescein, 0.2% in ethanol c) iodine atmosphere

SOLVENT SYSTEMS

| | | |
|---|---|---|
| a. | chloroform/methanol/water | 13:5:0.8* |
| b. | chloroform/methanol/ammonia 17% | 70:35:10* |
| c. | chloroform, saturated* | |
| d. | ether, saturated* | |
| e. | petroleum ether/ether/acetic acid | 70:30:1* |
| f. | butanol/acetic acid/water/acetic acid | 5:2:3* |
| g. | petroleum ether/ether/acetic acid | 50:50:1* |
| h. | ethyl acetate saturated with water* | |
| i. | ethyl acetate/chloroform/ammonia 17% | 98:6:1* |
| j. | chloroform/methanol | 9:1*# |
| k. | chloroform/methanol | 8:2*# |

-continued

| | |
|---|---|
| l. ether/benzene/ethanol/acetic acid | 40:50:2:0.2* |
| Rf values were determined at 20° C. | |

*TLC; #Column

COLUMN CHROMATOGRAPHY

Three methods were used for separation of palmitoylated (or other fatty acid acylated) TRIS constructs:

i) LH SEPHADEX

SEPHADEX LH 20 (PHARMACIA, Fine Chemicals) was packed into glass columns 1×25 cm) and samples eluted with chloroform/methanol mixtures at a rate of 1 ml/min. Fractions (5 ml) were collected and their contents analysed by TLC. Separation is by size.

ii) SILICA GEL COLUMN

Samples were loaded onto a silica gel column (BDH 60–120, size 2.6×30 cm) and eluted with chloroform/methanol mixtures (9:1 or 8:2 as required) at a rate of 2 ml/min. The effluent was monitored at 260 nm (ETP KORTEC, K95 UV monitor), 5 ml fractions collected and tested by TLC. Separation is by charge and hydrophobicity.

iii) FLORISIL COLUMN for separation of neutral lipids (a gift from Dr. Fogarthy, CSIRO Div. of Food Preservation). Chromatography was in glass columns of 12 gr acid washed FLORISIL and eluted with hexane/ethyl ether mixtures according to Carroll, K. K. and Serdarevich, B. (1967) in "Lipid Chromatography Analysis" p.205–237, Dekker, N.Y. The effluent was monitored by TLC.

ANALYSES i) Elemental analyses (CHN ratio) were carried out by the Analytical Unit of the Chemistry Department, Research School of Chemistry Australian National University GPO Box 4, Canberra.

ii) $^{13}C$ and PROTON NMR SPECTRA were done by the CSIRO Division of Biomolecular Engineering, Parkville, Vic. 3052. The compounds of the present invention behaved as expected with a slow exchange of protons which are good indications of peptide bonds.

iii) GLC analysis for fat content were done by Analchem Consultants Pty. Ltd.

iv) HPLC. Analytical HPLC of the N-protected amino acid-TRIS compounds were carried out using Millipore Waters HPLC equipment 6000A series solvent delivery system, connected to a Lambda Max Spectrophotometer Model 480, an Automated Gradient controller and Model 746 Data Module. Analytical HPLC was performed on a 100×8 mm NovaPak $C_{18}$ reverse phase radial pack cartridge and eluted at a flow rate of 2–3 ml/min. with a triethylamine phosphate pH3/acetonitrile gradient. The eluted substances were detected spectrophotometrically at 254 nm. The program used was a 20–100(6)5'(2) where 20–100 is the % acetonitrile at the beginning and end; (6) is the gradient program (6 is linear); 5' is time in minutes; (2) is the flow in ml/min.

Preparative HPLC

Separations were performed on a Millipore Waters Prep500 HPLC. The column was PrepPAK 500-$C_{18}$ (125A and 55–105 micron particle size) and the eluant was various concentrations of aqueous ethanol at 100 ml/min. Some separations required the addition of acetic acid at 1 ml/L.

PROTEASE TREATMENT OF Z-Ala-TRIS, Z-Gly-TRIS and Z-Leu-Arg-TRIS

Z-Gly-TRIS and Z-Ala-TRIS were incubated with papain, and Z-Leu-Arg-TRIS with trypsin, to test that the action of proteolytic enzymes could regenerate the starting compounds Z-Gly-OH, Z-Ala-OH and Z-Leu-Arg-OH respectively.

i) Activation of Papain 50 ul of a suspension of papain (25 mg/ml, Sigma) was incubated with 20 mm aqueous solution of EDTA (50 ul); 1 Molar solution of mercaptoethanol (25 ul); 50 mM triethylamine (25 ul); and water (100 ul) at 37° C for 30 min.

ii) Digestion Examples a) Papain. Z-Ala-TRIS in 50 mmolar phosphate buffer pH 6.5 (650 ul), 20 mM ethylene-diamise-tetra-acetic acid (100 ul) and water to 1 ml. Activated papain (5mg/ml) was added to a final enzyme/substrate ratio of 1:50. The reaction was followed by HPLC on $C_{18}$ reverse phase columns and the hydrolysis product identified by co-chromatography with standards.

Blanks were incubated as above using water instead of enzyme solution.

b) Trypsin. Z-Leu-Arg-TRIS was incubated at a concentration between 2 and 10 mg/ml in 0.2M ammonium hydrogen carbonate. Freshly prepared TPCK trypsin (1 mg/ml in water) was added to the solution giving a final enzyme/substrate ratio of 1:50. Samples were incubated at 37° C. and aliquots examined by reverse phase HPLC. Additional amounts of enzyme were added as required.

RESULTS i) Z-Ala-TRIS and Z-Gly-TRIS.

HPLC was used to monitor the progress of enzymatic hydrolysis. Both Z-Ala-TRIS and Z-Gly-TRIS were hydrolysed by papain, albeit very slowly. The main product was identical with Z-Ala-OH and Z-Gly-OH respectively by co-chromatography (i.e. spiking). This is a check that the type of linkage between the protected amino acid and TRIS is the same in the products made by method A and B (see below) and that it is most likely an amide bond. In addition we have the evidence from the NMR analysis of Z-Ala-TRIS (incubation method) that the bond is an amide linkage. Also, elemental and GLC analyses on fatty acid derivatives indicate three fat molecules per molecule of TRIS Indicating the presence of three OH groups on the amino acid-TRIS derivative used in the esterification.

ii) Z-Leu-Arg-TRIS was hydrolyzed slowly with trypsin. The product of hydrolysis was shown to be identical with an authentic sample of Z-Leu-Arg-OH by co-chromatography on HPLC.

Figure 1:
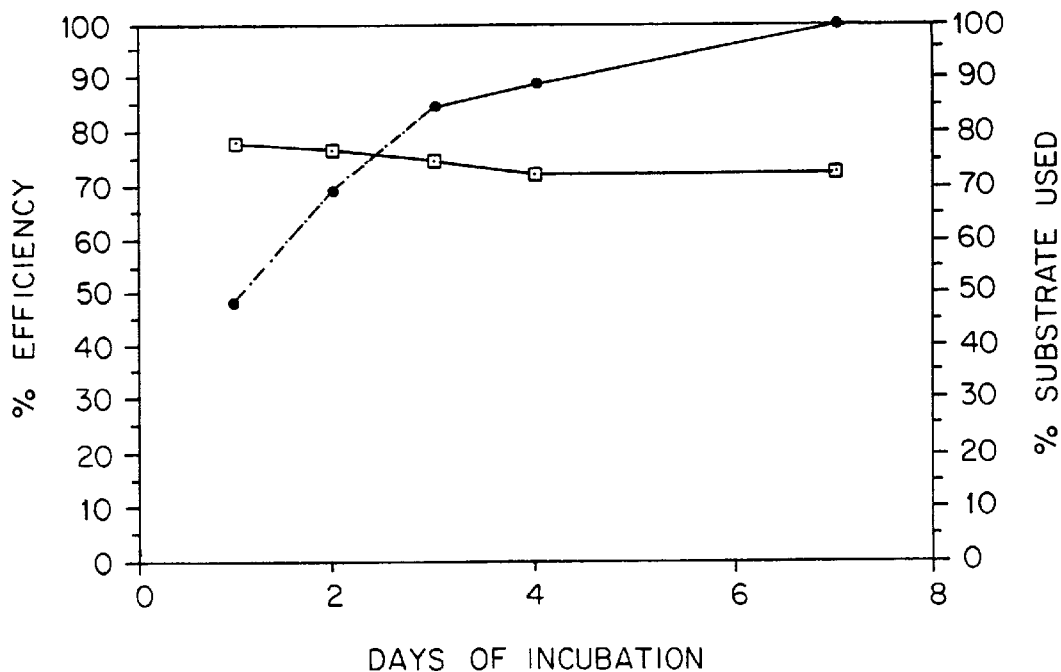
FIG. 1 shows a time profile of Z-Ala-OMe plus TRIS incubated at 60° C., pH8 in 60% DMF (— —□— —) percentage efficiency; (—♦—) percentage substrate used after 7 days.
Figure 2:
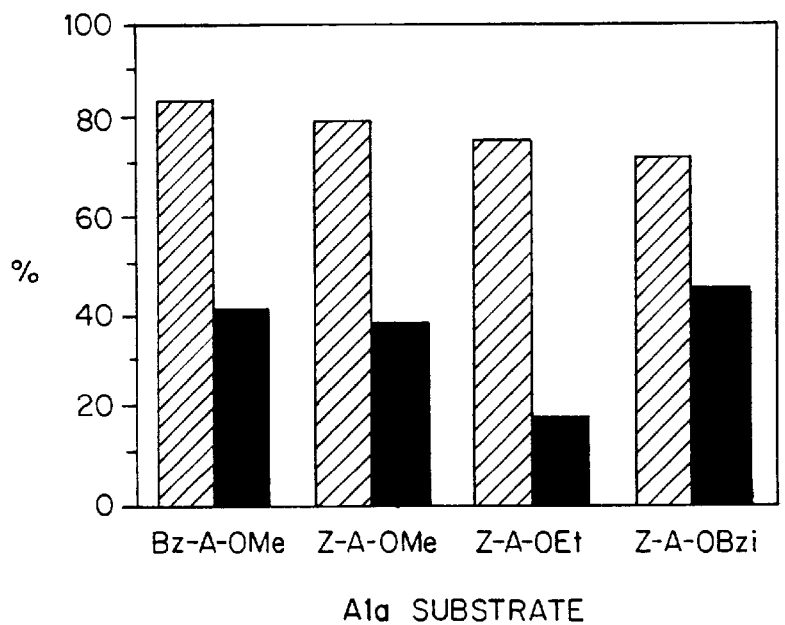
FIG. 2 shows substrate preference; 60° C. incubation for 18 hours, % efficiency (—▨—) and substrate used (—■—) vary with ester type and the nature of the amino terminal blocking group.
Figure 3:
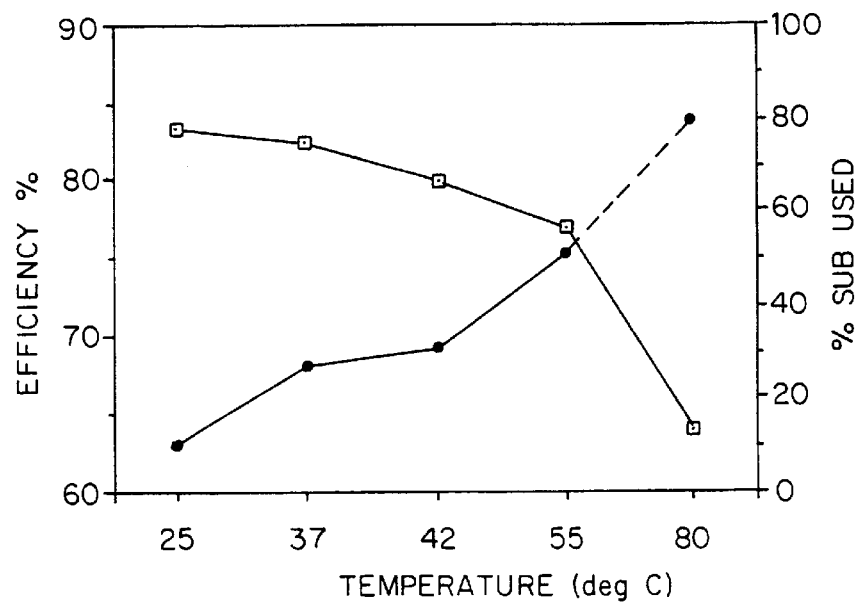
FIG. 3 shows temperature profile: BZ-Ala-CMe plus TRIS; 60% DMF pH 8.0 18 hours (—♦—) percentage substrate used; (— —□— —) percentage efficiency)
Figure 4:
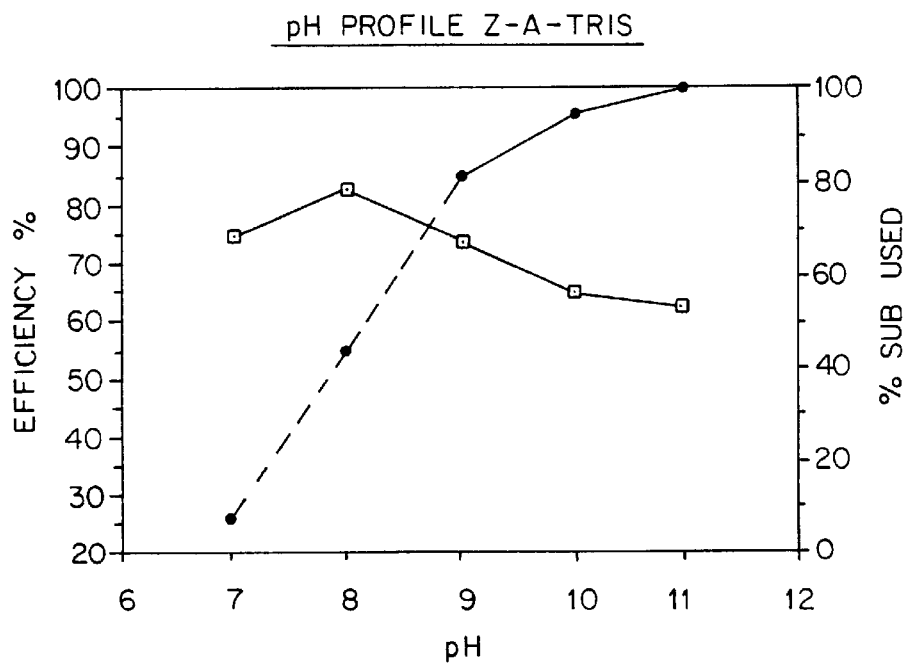
FIG. 4 shows pH profile Z-Ala-TRIS; 60% DMF incubated 2 days 60° C. (— —□— —) efficiency; (—♦—) percentage substrate used.

The amino acid-TRIS compounds were made by incubation of the N-protected amino acid esters and peptide esters with TRIS in 60% aqueous DMF at elevated temperature (see incubation method). A typical reaction time profile is shown in FIG. 1, effect of Z versus BZ plus ester types are shown in FIG. 2, temperature profile in FIG. 3, pH profile in FIG. 4 and DMF profile in FIG. 5.

As additional proof that the amino acid to TRIS linkage was a true amide bond, Z-Ala-TRIS and Z-Gly-TRIS were prepared by both the "incubation procedure" and normal organic chemistry methods for comparison by TLC. Tripalmitoylated forms of these two compounds were also prepared and compared by TLC. In a recent work by Otvos et al on the solid phase synthesis of certain glycopeptides (Peptide Research, 1989, 2, 362) the observation was made that in coupling of amino acids to carbohydrates unprotected hydroxyl groups are mostly unaffected when the symmetrical anhydride method is used. Symmetrical anhydrides of Z-Ala-OH and Z-Gly-OH were prepared and reacted with large excess of TRIS. The major products were indistinguishable by HPLC, TLC and CHN ratio from Z-Ala-TRIS and Z-Gly-TRIS prepared by the incubation method. Accordingly, we are confident that this method will only interact with the $NH_2$-group of TRIS and not any of the CH$_2$OH groups. It is also to be noted that only one synthetic compound is evident during the incubation method.

EXAMPLES

1. PREPARATION OF Z-AMINO ACID-TRIS AND ETHANOLAMINE COMPOUNDS

METHOD A—CHEMICAL SYNTHESIS (SYMMETRICAL ANHYDRIDE METHOD)

Example 1

Z-Ala-TRIS

The title compound was produced from Z-Ala-OH via the symmetrical anhydride procedure (Schussler, H., Zahn, H., Chem Ber. 95, p.1076 (1962) and Bodansky, M., and Bodansky, A. (1984) "The Practice of Peptide Synthesis". p.102, Springer-Verlag).

Z-Ala-OH (8 g) in DCM (50 ml) and a few drops of DMF was reacted with DCC(4.2 g) to form the symmetrical anhydride. The DCU so formed was filtered off and the solvent removed in vacuo. The residue was dissolved in DMF (50 ml) and added to a solution of TRIS in DMF (10 g/80 ml) and stirred at room temperature for 16 hours.

Purification of the title compound was by preparative HPLC which yielded an analytically pure white product. Yield 2.90 g (49% theory); Rf 0.49 (solvent h) and 0.78 (solvent b), and Rt 5.19' on HPLC. Anal. calc. for C$_{15}$H$_{22}$N$_2$O$_6$: C55.20, H6.80, N8.58. Found C55.28, H6.87, N8.13. The compound had identical characteristics to that formed by the "Incubation Method"—Method B (see Example 3).

Example 2

Z-Gly-TRIS

Z-Gly-TRIS was prepared in the same manner as Example 1 i.e. from Z-Gly-OH (7q) and purified by preparative HPLC. Yield 1.50 g (29% theory). The resulting Z-Gly-TRIS was chromatographically identical with the corresponding compound made by method B (see Example 4). Rf 0.36 (solvent h) and 0.66 (solvent b), and Rt 4.97' on HPLC. Anal. calc. for C$_{14}$H$_{20}$N$_2$O$_6$: C53.84, H6.45, N8.97. Found C54.53, H6.84, N8.85.

METHOD B. INCUBATION METHOD

Example 3

Z-Ala-TRIS 5.04 g of Z-Ala-Ome (50 mmole) was added to 20.37 g. of TRIS (400 mmole) in DMF (252 ml) and water 168 ml) and incubated at 55° C. at pH 9.0. The reaction was monitored by HPLC which showed that after four days the conversion to the title compound was complete with a 65% efficiency as determined by HPLC.

Purification by preparative HPLC gave an analytically pure Z-Ala-TRIS as a white powder. Rf 0.49 (solvent h) and 0.79 (solvent b). HPLC Rt was 5.19 minutes. Anal. calc. for C$_{15}$H$_{22}$N$_2$O$_6$: C55.20, H6.80, N8.58. Found C56.02, H7.03, N8.00. The structure was confirmed by NMR analysis.

Example 4

Z-Gly-TRIS 10.02 g of Z-Gly-OBzl was added to 32.4 g of TRIS in DMF (401 ml) and water (267 ml) and incubated at 60° C. at pH 9.0 for two days. Purification by preparative HPLC gave analytically pure Z-Gly-TRIS as a white powder. Yield 3.98 g (38.3% theory); Rf 0.36 (solvent h) and 0.66 (solvent b); HPLC Rt was 4.97'. Anal. calc. for C$_{14}$H$_{20}$N$_2$O$_6$ : C53.84, H6.48, N8.97. Found C54.15, H6.56, N8.68. The structure was confirmed by NMR analysis.

Example 5

Z-Leu-TRIS

Z-Leu-OMe (5 g) and TRIS (16.2 g) in DMF (200 ml) and water (134 ml) was incubated at pH 8.0 and 55° C. in the manner previously described (Example 3).

Purification by preparative HPLC gave 3.60 g (54% of theory) of analytically pure title product; Rf 0.62 (solvent h) and 0.25 (solvent i); HPLC Rt 6.37'.

Example 6

Z-Leu-Arg-TRIS

Z-Leu-Arg-Ome (5.17 g) and TRIS (10.67 g) in a solution of DMF (132 ml) and water (88 ml) was incubated at 55° C. for seven days in the manner previously described. The efficiency of the reaction was 55% by HPLC. Pure product was isolated by preparative HPLC. TLC Rf 0.70 (solvent f) and 0.02 (solvent b); Rt 5.37'.

Example 7

BOC-Ala-Ile-Phe-TRIS 8.6 g of BOC-Ala-Ile-Phe-OMe was added to 20 g of TRIS in DMF (240 ml) and water (160ml). The mixture was incubated at 55° C. for four days (yield by HPLC 66%) and the title compound purified by preparative HPLC to give the analytically pure product (yield 1.4 g; 14% theory); Rf 0.50 (solvent h) and 0.85 (solvent b); HPLC Rt 6.55'. Anal. calc. for C$_{26}$H$_{45}$N$_4$O$_8$ : C57.65, H8.37, N10.34. Found C58.01, H8.12, N9.57.

Example 8

Z-Ala-ETHANOLAMINE

Z-Ala-OEt (5.73 g) was incubated in DMF (273 ml) and water (91ml) at 50° C. with 91 ml ethanolamine at pH 11.

The reaction was monitored by HPLC and after twenty hours the formation of the title compound was complete with 82% efficiency by HPLC. Preparative HPLC yielded a chromatographically pure product (2.26 g: 38% theory); Rf 0.50 (solvent h) and 0.82 (solvent b); HPLC Rt 5.10'.

Example 9

FORMATION OF AMINO ACID—TRIS COMPLEXES

Comparative reactions were run using Z-Leu-OMe; Z-Ala-OMe; Bz-Tyr-OEt; Z-Ala-OBzl; Z-Arg-OMe; Z-Val-OMe and Bz-Arg-OMe. The efficiency of the reaction of these compounds with TRIS and the rate at which the reaction proceeded are set out in Tables 1 and 2, respectively.

TABLE 1

| Substrate | Efficiency 1 Day Incubation | Efficiency 3 Day Incubation | Efficiency 7 Day Incubation |
|---|---|---|---|
| Bz—Tyr—OEt | 81% | 79% | — |
| Z—Leu—OMe | 81% | 76% | 76% |
| Z—Ala—OMe | 78% | 77% | 73% |
| Z—Ala—OBzl | 73% | 71% | 69% |
| Z—Arg—OMe | 72% | 72% | 67% |
| Z—Val—OMe | 66% | 61% | — |
| Bz—Arg—OMe | 58% | 75% | — |

TABLE 2

| Substrate 50 mm | Rate (Used) 1 Day Incubation | Rate (Used) 3 Day Incubation | Rate (Used) 7 Day Incubation |
|---|---|---|---|
| Bz—Arg—OMe | 68.51% | 86.12% | — |
| Z—Arg—OMe | 62.30% | 91.63% | 100% |
| Z—Ala—OMe | 48.16% | 83.87% | 100% |
| Z—Ala—OBzl | 43.98% | 86.53% | 94.8% |
| Z—Leu—OMe | 24.24% | 64.29% | 85.28% |
| BZ—Tyr—OEt | 22.89% | 52.15% | — |
| Z—Val—OMe | 4.19% | 22.40% | — |

Example 10

FORMATION OF Z-LEU-ARG-TRP-TRIS 5.28 grams of Z-Leu-Arg-Trp-OMO was added to 7.6 grams of TRIS in 160 mls of solvent consisting of 60% DMF and 40% $H_2O$. The reaction was allowed to proceed at 60° for four days at pH 10. Z-Leu-Arg-Trp-TRIS was recovered by preparative HPLC. Efficiency by HPLC—43%. Rf 0.72 (solvent f).

Example 11

FORMATION OF Bz-Tyr-Arg-Lys-TRIS 5.025 grams of Bz-Tyr-Arg-Lys-OE was added to 7.275 grams of TRIS in 150 mls. of solvent comprising 60% DMF and 40% $H_2O$. The reaction was allowed to proceed at 600 for four days 50% yield by HPLC and Bz-Tyr-Arg-Lys-TRIS was recovered by preparative HPLC.

2. PREPARATION OF FATTY ACID COMPLEXES

Example 12

Z-Ala-TRIS-TRIPALMITATE

A solution of palmitic acid (8.10 g) in chloroform (100 ml) was added to a stirred solution of Z-Ala-TRIS (2.75 g) in chloroform (60 ml) and DMF (15 ml) and the mixture cooled in ice. After dropwise addition of 6.50 g of DCC in chloroform (30 ml) followed by 0.4 g of DMAP in chloroform (10 ml), stirring was continued at 0° C. for two hours and then at room temperature for 18 hours. The esterification reaction was monitored by TLC (solvent systems b, h, i and j). The resulting DCU was filtered off and the chloroform solution serially washed with water; 10% aqueous citric acid; water; 10% aqueous sodium hydrogen carbonate and water. The solution was dried over sodium sulphate and the solvent evaporated under reduced pressure. The crude product was purified by chromatography by three different methods:—LH Sephadex; silica gel and Florisil. All techniques gave Analytically pure products that gave a single spot on TLC; Rf 0.72 (solvent g) and Rf 0.29 (solvent e). Yields were 62.0%, 63.8% and 68.5% respectively. Anal. chem. for $C_{63}H_{112}N_2O_9$ : C72.65, H10.84, N2.69. Found C72.58, H11.22, N2.31.

Fat (palmitic acid) content by GLC analysis was 70.1% indicating full esterification of all three hydroxyl groups of the Z-Ala-TRIS (Theory 68.7%). NMR results were consistent with the proposed structure. Products made with Z-Ala-TRIs prepared by both the chemical and incubation methods yielded analytically indistinguishable products.

Example 13

Z-Gly-TRIS-TRIPALMITATE 0.94 g of Z-Gly-TRIS was reacted with 3.30 g of palmitic acid; 2.5 g of DCC and 0.12 g of DMAP (as per Example 12) to give a crude sample of the title product, 2.05 g, 67% Theory. Purification on LH Sephadex and silica gel gave analytically pure product in 43% and 45% yield respectively; TLC Rf 0.18 (solvent e) and 0.85 (solvent 1).

Fat (palmitic acid) content by GLC analysis was 70% indicating full esterification of all three hydroxyl groups of the Z-Gly-TRIS (Theory 69.6%). NMR results were consistent with the proposed structure. Products made with Z-Gly-TRIS prepared by both the chemical and incubation methods yielded analytically indistinguishable products.

Example 14

Z-Leu-TRIS-TRIPALMITATE 1.10 g of Z-Leu-TRIS was reacted with 3.30 g of palmitic acid; 2.5 g of DCC and 0.12 g of DMAP (as per Example 12) to give a crude sample of the title product. Purification on a silica column yielded 1.78 g (54.9% Theory) of analytically pure product; TLC Rf 0.90 (solvent g) and 0.87 (solvent k). Anal. calc. for $C_{67}H_{121}N_2O_9$ : C73.08,m H11.06, N2.58. Found C73.74, H11.52, N2.29. Fat content 66.0% (Theory 66.1%).

Example 15

Z-Ala-TRIS-MYRISTATE

Z-Ala-TRIS (326 mg) was reacted with myristic acid (914 mg) in chloroform in a similar manner to Example 10. DCC (825 mg) and DMAP (40 mg) in cold DCM (10 ml) was added and stirred for two hours at 0° C. followed by 16 hours at room temperature. Initial purification yielded 720 mg crude product. Precipitation from DCM/acetonitrile yielded 640 mg. (66.9% of the theoretical) of the title product. TLC gave a single spot of Rf 0.63 (solvent g) and 0.29 (solvent e).

Example 16

Z-Ala-TRIS-TRILAURATE 326 mg of Z-Ala-TRIS and 801 mg lauric acid was reacted with 825 mg DCC and 45 mg DMAP in a manner similar to that described for Example 12. Evaporation of the solvent yielded 710 mg of crude title product. This was further purified on a Florisil column using the hexane-ethyl ether solvent mixtures as eluants. 420 mg (49.9% of theoretical) of the title compound was recovered; TLC Rf 0.59 (solvent g) and 0.27 (solvent e).

Example 17

Z-Ala-TRIS-TRICAPRATE 326 mg of Z-Ala-TRIS and 464.7 mg of capric acid (n-decanoic acid) was reacted with 825 mg of DCC and 45 mg of DMAP in DCM in a manner described in Example 13. Purification on Florisil with hexane/ether and methanol gave chromatographically pure title product; yield 480 mg (61% Theory); Rf 0.54 (solvent g) and 0.25 (solvent e). Anal. calc. for $C_{45}H_{76}N_2O_9$ : C68.49, H9.71, N3.55. Found C68.96, H10.230, N3.18. Fat content by GLC was 63% (Theory 58.9%).

Example 18

Z-Ala-TRIS-MONOPALMITATE 700 mg of Z-Ala-TRIS was reacted with 500 mg palmitic acid and 410 mg DCC and 20 mg DMAP in the manner similar to that described in Example 12 except a 1.3 molar excess of reagents was used instead of the usual 4 molar excess to generate a construct with predominantly one fatty acid attached: some di and tri-palmitoylated product would alto be expected. Yield of crude, mixed products 1.12 g (Theory 1.20 g).

Fractionation on Florisil gave three major products in the ratio of 0.27:1:1 with Rf's on solvent g of 0.73; 0.26 and 0.0 respectively. Fractions 1 and 2 are isomeric dipalmitate derivatives analysing by GLC as containing two fat molecules relative to Z-Ala-TRIS (56% and 59% resp.; Theory 59.6%) while Fraction 3 was consistent with being a mono-palmitate derivative (fat content was 40%; Theory 42.5%). The yield by weight of Fraction 3 was 208 mg (24.5% Theory).

Example 19

BOC-Ala-Ile-Phe-TRIS-TRIPALMITATE

BOC-Ala-Ile-Phe-TRIS-tripalmitate was prepared in a similar manner to Example 12 from a solution of BOC-Ala-Ile-Phe-TRIS (500 mg in 30 ml chloroform; 5 ml DMF); palmitic acid (1.1 g in 20 ml chloroform), 825 mg of DCC in 10 ml chloroform and DMAP (40 mg in 10 ml chloroform) at 0° C. for 2 hours and at room temperature for 16 hours.

After the removal of DCU, the chloroform solution was washed as previously described (water, citric acid, water, sodium hydrogen carbonate, water). After the removal of solvent, the oily residue was dried (Crude yield 1.66 g).

The crude product was dissolved in hexane and a portion of the solution purified on a Florisil column. Hexane: ether solvent mixtures removed the unreacted palmitic acid and other impurities. The title product was then eluted with chloroform:methanol 50:50 (150 ml). The product was obtained as an oil, which was lyophilised from t-butylalcohol. The white fluffy compound (770 mg; 66.4% Theory) gave a single spot on TLC; Rf 0.44 (solvent g) and 0.13 (solvent e). Anal. chem. for $C_{74}H_{135}N_4O_{11}$ : C70.71, H10.83, N4.46. Found C70.72, H10.78, N4.14. Fat content by GLC was 58% (Theory 56.9%).

Example 20

Z-Ala-ETHANOLAMINE-MONOPALMITATE 540 mg of the Z-Ala-ethanolamine was reacted with 670 mg palmitic acid, 540 mg DCC and 32 mg of DMAP in DCM and DMF as per Example 12. The mixture was evaporated to dryness and purified on Florisil. 219 mg of product (20% theory) was isolated. TLC Rf 0.16 (solvent g), 0.14 (solvent c, twice) and 0.12 (solvent d).

Example 21

MITOGENIC EFFECTS OF Z-Ala-TRIS-TRIPALMITATE AND Ala-TRIS-TRIPALMITATE

Lipopeptides of the type $Pam_3$-Cys-Ser-$(Lys)_4$ and $Pam_3$-Cys-Ala-Gly are potent lymphocyte and macrophage activators (e.g. Reitermann et al., Biol. Chem. Hoppe-Seyler, 370, pp343–352). These compounds have also been shown to induce tumour cytotoxicity (Hoffmann et al 1989. Biol. Chem. Hoppe-Seyler, 370, pp575–582) in murine bone marrow derived macrophages.

The mitogenic effects of two of our constructs, Z-Ala-TRIS-Tripalmitate and Ala-TRIS-Tripalmitate were examined as follows:

INCORPORATION OF $^3$H-THYMIDINE $^3$H-thymidine incorporation experiments were carried out in Linbro-Titertek microtitre plates (Flow Laboratories, Inc., U.S.A.) following the method of L. Bradley in "Selected Methods of Cellular Immunology" (1980) Eds. B. B. Mishell and S. M. Shiigi; Publisher. W.H. Freeman and Co., U.S.A. pp156. The tests were carried out externally by Dr. D. Rathjen of Peptide Technology Ltd., Dee Why, N. S. W.

Cell lines tested were:
1. RD10; a B-cell lymphoma (obtained from the Centre for Immunology, Sydney University, Sydney, NSW.
2. U937; a human monocyte-like3 histiocytic lymphoma (source: American Tissue Culture Collection).

METHOD (EXAMPLE)

RD10 cells (at a cell density $5\times10^5$/ml, 100 ul/well) were cultured for 20 hours at 37° C. with 5% $CO_2$ in RPMI 1640 medium, supplemented with 10% Fetal Calf. Serum. Samples to be tested were mixed and sonicated with this medium at a concentration of 5000, 500.50 and 5 ug/ml and 100 ul aliquots added to the cells. The cells were pulsed with 0.5 uCi/well of $^3$H-thymidine and the plates incubated for four more hours before harvesting (Titertek Skatron harvester, Lier, Norway). Incorporated radioactivity was measured by liquid scintillation counting. All assays were performed in triplicate.

RESULTS

FIGS. 6 and 7 summarize the results.

$^3$H-thymidine uptake by RD10 cells showed a 3–4 fold increase in cell proliferation compared to control. This is in the range of other known mitogenic compounds e.g., phytohaemagglutinin gives a 5–10 fold increase under these conditions. The samples containing Ala-TRIS-Tripalmitate, where the N-terminal of the Alanine is free, showed a slightly diminished response compared with Z-Ala-TRIS-Tripalmitate.

Thymidine incorporation of the U937 cells was, in slight contrast, close to control, and at higher concentrations indicated slight cytotoxic effects. As in the experiments using B-cells, Ala-TRIS-Tripalmitate samples showed slightly diminished responses compared with Z-Ala-TRIS-Tripalmitate.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

We claim:

1. A compound of the following formula:

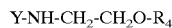

in which Y represents an amino acid, or peptide and $R_4$ represents a fatty acid having a carbon chain of 3 to 18 carbon atoms.

2. A compound as claimed in claim 1 in which the fatty acid has a carbon chain of 10 to 18 carbon atoms.

3. A compound as claimed in claim 2 in which the fatty acid has 16 carbon atoms.

4. A compound as claimed in claim 1 in which Y is cysteine.

5. A method of producing a compound according to claim 1 comprising the steps of:

(1) adding an N-protected amino acid or peptide ester to ethanolamine in the presence of 60% aqueous dimethylformamide to form a mixture, (2) incubating said mixture at a temperature in the range of about 55° to 60° and a pH of about 9 for about 1–7 days wherein said ethanolamine is linked to the C-terminal of said amino acid or peptide, (3) adding a fatty acid to said mixture while stirring at 0° for about 2 hours, and (4) continuing stirring at room temperature until the reaction is completed.

* * * * *